(12) United States Patent
Bees

(10) Patent No.: US 7,234,815 B2
(45) Date of Patent: Jun. 26, 2007

(54) OPTICAL VIEWING DEVICE HAVING AN APPARATUS FOR PARTIAL REDUCTION OF THE ILLUMINATION INTENSITY

(75) Inventor: Bryan Bees, Bristol (GB)

(73) Assignee: Leica Microsystems (Switzerland) AG, Heerbrugg (CH)

( * ) Notice: Subject to any disclaimer, the term of this patent is extended or adjusted under 35 U.S.C. 154(b) by 88 days.

(21) Appl. No.: 10/078,383

(22) Filed: Feb. 21, 2002

(65) Prior Publication Data

US 2002/0113941 A1 Aug. 22, 2002

(30) Foreign Application Priority Data

Feb. 21, 2001 (DE) ................. 101 08 254

(51) Int. Cl.
*A61B 3/10* (2006.01)
*A61B 3/00* (2006.01)

(52) U.S. Cl. ..................... 351/213; 351/221

(58) Field of Classification Search ............ 351/205, 351/213, 216, 221, 222, 233, 236; 359/722–723, 359/889; 362/293; 349/18, 104, 106; 353/84; 606/4–6

See application file for complete search history.

(56) References Cited

U.S. PATENT DOCUMENTS

| 4,013,347 | A | * | 3/1977 | Nakamura | 359/724 |
|---|---|---|---|---|---|
| 4,715,704 | A | | 12/1987 | Biber et al. | 351/207 |
| 4,810,084 | A | * | 3/1989 | Nyui | 351/206 |
| 4,878,748 | A | * | 11/1989 | Johansen et al. | 351/49 |
| 4,936,673 | A | | 6/1990 | Mauersberger | 351/214 |
| 4,952,046 | A | * | 8/1990 | Stephens et al. | 351/163 |
| 4,991,954 | A | * | 2/1991 | Akiyama | 351/221 |
| 5,029,010 | A | * | 7/1991 | Shiraishi | 359/723 |
| 5,442,487 | A | * | 8/1995 | Mizuno | 606/4 |
| 5,541,779 | A | * | 7/1996 | Choi | 359/888 |
| 5,555,040 | A | | 9/1996 | Kaneko | |
| 5,751,395 | A | * | 5/1998 | Thall | 351/221 |
| 5,801,807 | A | * | 9/1998 | Satake et al. | 351/221 |
| 5,894,337 | A | * | 4/1999 | Okinishi et al. | 351/205 |
| 6,056,739 | A | * | 5/2000 | Klopotek | 606/5 |
| 6,126,287 | A | * | 10/2000 | Akiyama | 351/221 |
| 6,271,968 | B1 | * | 8/2001 | Dobrowolski et al. | 359/583 |
| 6,297,912 | B1 | * | 10/2001 | Goto | 359/676 |
| 6,305,801 | B1 | * | 10/2001 | Kerns et al. | 351/162 |
| 2002/0036763 | A1 | * | 3/2002 | Krikke et al. | 355/67 |

FOREIGN PATENT DOCUMENTS

| DE | 88 08 871.5 | 10/1988 |
|---|---|---|
| DE | 93 01 448.1 | 4/1993 |
| DE | 42 14 445 A1 | 11/1993 |
| DE | 195 21 971 A1 | 12/1995 |
| JP | 9-94255 A | 4/1997 |
| JP | 9-173351 A | 7/1997 |

\* cited by examiner

Primary Examiner—Scott J. Sugarman
(74) Attorney, Agent, or Firm—Foley & Lardner LLP

(57) ABSTRACT

The invention concerns an optical viewing device which incorporates a spectral filter to partially reduce the intensity or wavelength(s) of light transmitted to a specific region of a specimen which may be a human eye. The reduction in light intensity or wavelength may be variable across the filter and may be accomplished in an intensity-dependent or a wavelength-dependent manner.

35 Claims, 4 Drawing Sheets

OPTICAL VIEWING DEVICE HAVING AN APPARATUS FOR PARTIAL REDUCTION OF THE ILLUMINATION INTENSITY

CROSS REFERENCE TO RELATED APPLICATIONS

This invention claims priority of German Patent Application DE 101 08 254.1, the entirety of which is incorporated herein by reference.

BACKGROUND OF THE INVENTION

1. Field of the Invention

The invention concerns an optical viewing device, such as for example a surgical (stereo) microscope, having an apparatus for partial reduction of the illumination intensity, such as an eclipse filter. An "eclipse filter" is understood to be a spectral filter in an illuminating beam which fully or partially reduces the illumination intensity in a specific light wavelength range.

2. Description of the Related Art

Reduction of the illumination of a specific spatial region of a specimen, by means of a stop, is more frequently being used in a variety of applications so that light sensitive surfaces, of the specimen can be protected from excessively strong radiation. These stops are generally configured to swing into and out of an illuminating beam thereby providing complete and/or partial darkening of the illuminating beam in a specific spatial region which is to be protected from the light.

German Patent Document DE 93 01 448 U, which is incorporated herein by reference, discloses a filter system. The filter system, which includes individual filters possessing different diameters, provides for a partial darkening in specific spatial regions. This darkening is not wavelength-dependent in the visible light region between 400 and 700 nm. In addition, German Patent Document DE 88 08 871 U, which is also incorporated herein by reference, provides a diffusion plate for slit lamp devices which plate creates a preferred direction in the scattering characteristic. Further, U.S. Pat. No. 4,715,704, which is also incorporated herein by reference, describes a light trap having a centrally darkened region.

Although the aforementioned patents have improved the art, various disadvantages remain. First, the reduction in light intensity is accomplished either in binary fashion (i.e., the reduced-light specimen region either appears dark to the user or is visible at full brightness), or there is a graduated filter effect which is not optimized in terms of light color; this can have negative effects on a specimen, for example on a patient's eye. Second, to make the reduced-light region visible in true color to the viewer, it is necessary to remove the stop thereby completely illuminating the specimen; such illumination may damage the specimen. Third, because of the fixed positioning of the stop in the illuminating beam, the shape and/or the attenuated illuminating beam cannot be varied. Fourth, damage to the specimen, for example to the patient's eye, usually does not occur in a similarly hazardous fashion over the entire range of light wavelengths. Rather, damage occurs only in a specific wavelength range, for example from 420 nm to 470 nm (or even up to 495 nm). In addition, below 400 nm, it is unnecessary to filter out all wavelengths.

In light of the aforementioned deficiencies in the prior art, a new apparatus is needed for reducing the intensity of light which is directed toward sensitive regions of a specimen which may be injured by excessively strong radiation.

SUMMARY OF THE INVENTION

A first aspect of the invention addresses an optical device which includes a light source emitting light along an illuminating beam having a two-dimensional cross-sectional area. The device also includes a main objective and a spectral filter positioned between the light source and the main objective. The spectral filter is adapted to reduce, without eliminating, the intensity of the light emitted by the light source in a specific region, the specific region being a subsection of the two-dimensional cross-sectional area of the illuminating beam. In addition, the spectral filter may be any one or more of a thin film, an LCD, and an electrochromic film.

With respect to the device, the reduction of the light intensity by the spectral filter may be wavelength-dependent and/or intensity-dependent. In addition, at least one region of the spectral filter absorbs a portion of the intensity produced by a specific wavelength $\lambda$ which is in a range selected from the group consisting of the wavelengths from 420 to 470 nm, wavelengths below 400 nm, wavelengths injurious to a human's retina, and wavelengths injurious to a human's cornea.

The spectral filter of the invention may absorb a portion of the light being transmitted by the light source having at least one wavelength. For each wavelength, a portion of which is absorbed, absorption edges may be defined between the specific region and the remainder of the cross-sectional area of the illuminating beam. Further, the absorption edges of at least one of the reduced-light intensity wavelengths may be flat in nature.

The spectral filter may be mechanically moved in its (x, y) plane and along the illuminating beam, i.e., the filter may be moved in up to three dimensions. Moreover, the movement may be controlled either manually or electronically. Further, if the spectral filter is vertically moved, the size of the specific region may be altered.

The spectral filter may have a disk-like shape and have a profile that includes a variable reduced-light intensity wavelength illumination region which varies from a central portion of the spectral filter to the outer rim of the spectral filter. In addition, in the central portion, the intensity of wavelengths between 420 nm and 470 nm may be reduced up to substantially 90% (e.g., 25%, 50%, and 75%) whereas in the outer rim, the intensity of the wavelengths between 420 nm and 470 nm may not be substantially reduced.

The light source preferably produces light having wavelengths between 420 nm and 470 nm. In addition, the spectral filter preferably reduces the intensity of the light emitted by the light source by between substantially 0% and 90%.

The illuminating beam produced by the light source is preferably adapted to be projected through the objective and onto a specimen. Further, if the illuminating beam reflected by the specimen is directed into an image protocol and the location of the spectral filter is controlled by means of a controller, the image protocol and the controller may be linked so that if the specimen moves, the controller will correspondingly move the spectral filter.

An (x, y) plane, defined by the spectral filter, may be oriented at an angle with respect to the illuminating beam. An angling of this nature can vary a degree in the light intensity reduction across the spectral filter with respect to the objective.

These and other features, aspects, and advantages of the present invention will become more apparent from the following description, appended claims, and accompanying exemplary embodiments shown in the drawings.

BRIEF DESCRIPTION OF THE DRAWINGS

The accompanying drawings, which are incorporated in and constitute a part of the specification, illustrate embodiments of the invention and together with the description, serve to explain the principles of the invention.

DETAILED DESCRIPTION OF THE PREFERRED EMBODIMENTS

Figure 1:
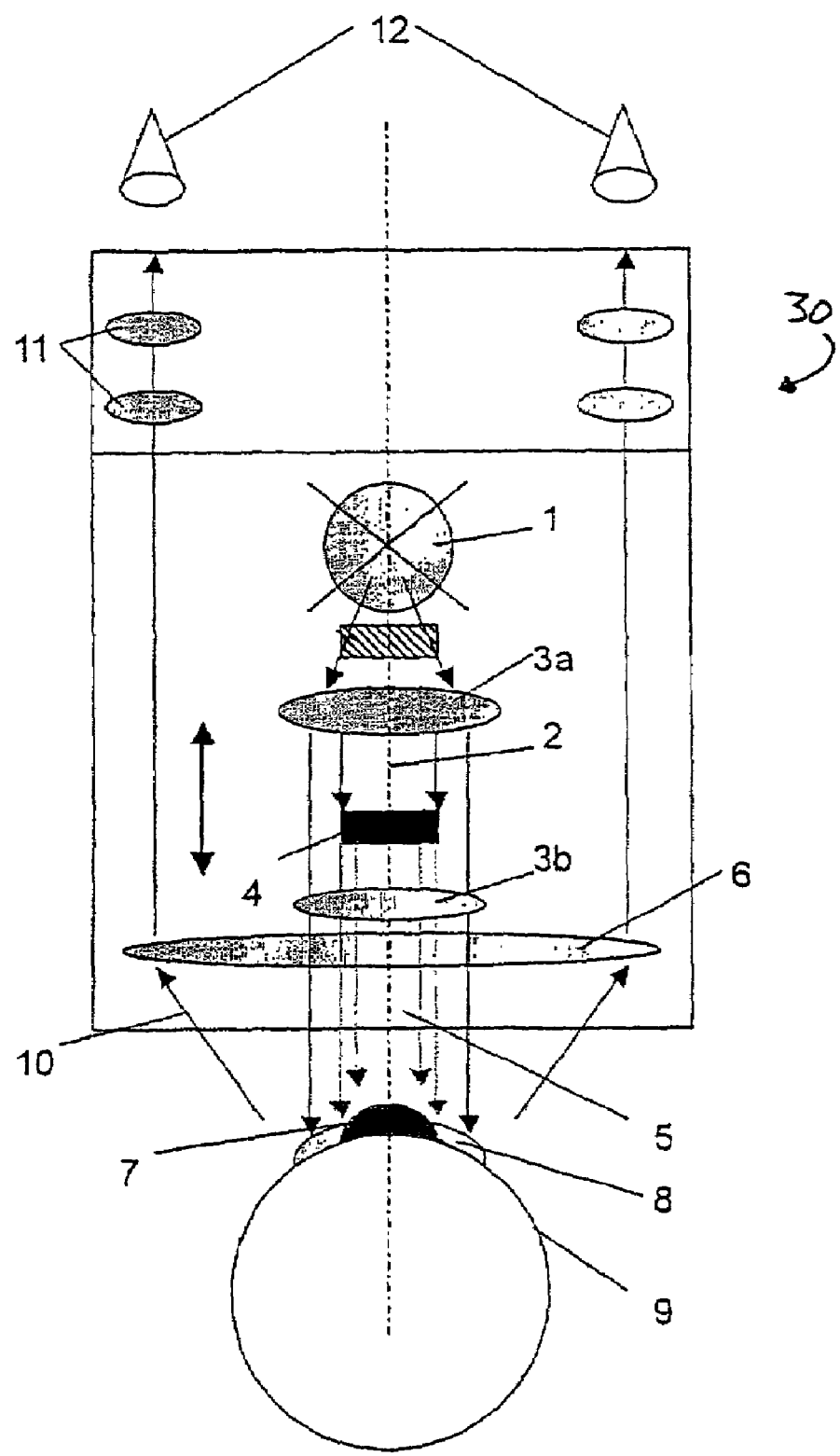
FIG. 1 symbolically shows the overall construction of an optical viewing device including a specimen beam, an eyepiece, and a viewer.

The apparatus described herein optimally protects a sensitive region of a specimen which may be, for example, a patient's eye. Moreover, this protection is possible regardless of (a) the three-dimensional shape of the specimen's sensitive region, or (b) the intensity at which injury occurs to the region of the specimen to be protected. This sensitive region is protected using, in the illuminating beam, a spectral filter that varies its filter effect in graduated or stepless fashion, for example as a function of distance from a central portion of the filter.

The spectral filter is of a defined spatial configuration. For example, the filter may possess the shape of the specimen to be protected. The spectral filter may additionally have a defined absorption and/or reflection which may be between, e.g., 0% and 90%, in particular in the light wavelength region between 420 and 470 nm. Moreover, the absorption and/or reflection may be defined to a particular range by means of thin films.

The filter is preferably spatially displaceable in three dimensions and divisible into fields having different absorption and/or reflection properties. In addition, the filter can be configured, e.g., as an LCD and/or as an electrochromic film thereby allowing it to be controlled electronically.

With the use of the spectral filter described herein many improvements and advancements over the prior art are possible. For instance, as a result of the light wavelength-dependent darkening of the specimen region to be protected, the specimen is protected from injury by means of optimized light colors. In addition, darkening is not performed such that either all or no light is transmitted to the specimen. Rather, the darkening is between, for example, 0% and 50%. The darkened region, therefore, remains continuously visible to the viewer in a specific non-hazardous light wavelength region.

If a particular region of the specimen surface is known to be injured at a specific light intensity, the intensity may be limited to be below that injury causing intensity. Similarly, if the specimen surface to be protected is only injured by specific wavelengths, the intensity in that region can be limited to exclude those wavelengths; however, those injury-causing wavelengths can be transmitted to other regions of the specimen.

As a result of the division of the spectral filter into different regions, different absorption profiles (i.e., intensity reduction as a function of wavelength) can be generated. Further, as a result of the spatial displaceability of the spectral filter, the protected region can be varied to a specific extent. In addition, by using thin films, it is possible to create any desired absorption profile for the light. Further, by using an LCD and/or electrochromic films, any desired absorption surfaces and/or absorption profiles can be created in electronically controlled fashion.

Reference will now be made in detail to the present preferred embodiments of the invention, examples of which are illustrated in the drawings. Wherever possible, the same reference numbers will be used throughout the drawings to refer to the same or like parts.

FIG. 1 symbolically shows the overall construction of an optical viewing device, which may be, for example, a surgical stereomicroscope. The viewing device 30 includes a light source 1, such as, for example, a lamp or the end of an optical waveguide. The light source 1 produces an illuminating beam 2 which is directed through an illuminating optical system comprising two lenses, 3a, 3b. A spectral filter 4 is preferably positioned between the lenses 3a, 3b of the optical system. However, it is to be understood that the spectral filter 4 could, for example, be positioned between the upper lens 3a and the light source 1.

A main objective 6 is positioned between the lower lens 3b and a specimen which may be, for example, a human eye comprising a pupil 7, an iris 8, and an eyeball 9. As a result of the spectral filter 4, the portion of the cross-sectional area of the illuminating beam 2 is diffused into a reduced-light intensity beam 5. The reduced-light intensity beam 5 is transmitted through the main objective 6 to a specific region of the specimen which may be subject to injury caused by light intensity and/or specific wavelengths of light. In addition, in response to the illuminating beam 2 and the reduced-light intensity beam 5, the specimen produces a beam 10 which is directed through the optical viewing device to an eyepiece 11 of a viewer 12.

The illuminating beam 2 emerging from light source 1 may be reduced in intensity in a specific two-dimensional region (x, y), in a manner dependent on the light wavelength, by way of the illuminating optical system 3a, 3b and the spectral filter 4 located therebetween. As a result, the intensity is reduced by means of spectral filter 4 over the specific light sensitive region, which may be, for example, the retina/cornea of a human eye. Alternatively, or in addition, the intensity of the light may be reduced based on the intensity of the light, i.e., the degree to which the spectral filter reduces the intensity may depend on the intensity. In this manner, the spectral filter may be wavelength-dependent and/or intensity-dependent.

Figure 2A:
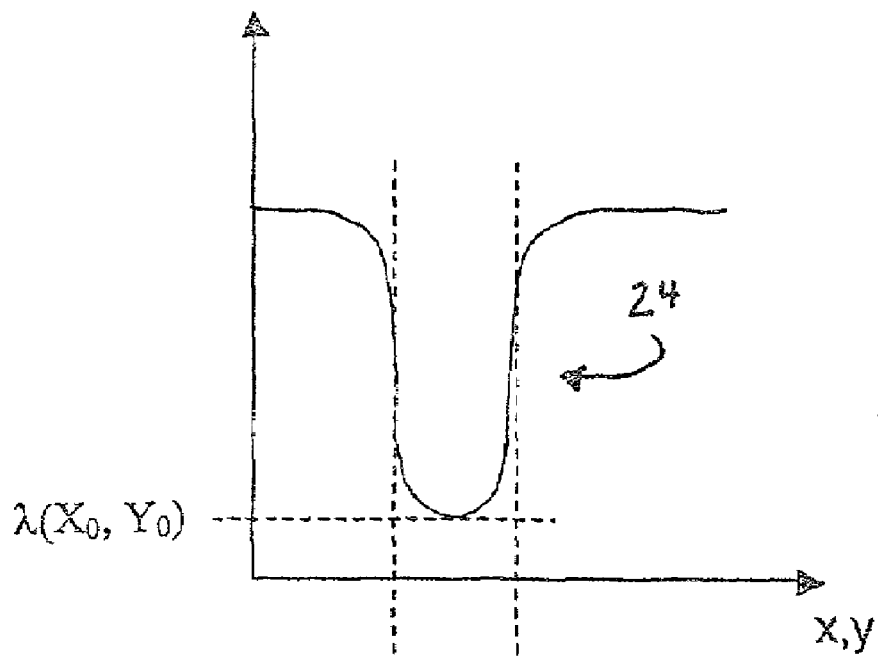
FIG. 2A is a graph of an intensity of a wavelength $\lambda$ as a function of a two-dimensional spatial region of a specimen.
Figure 2B:
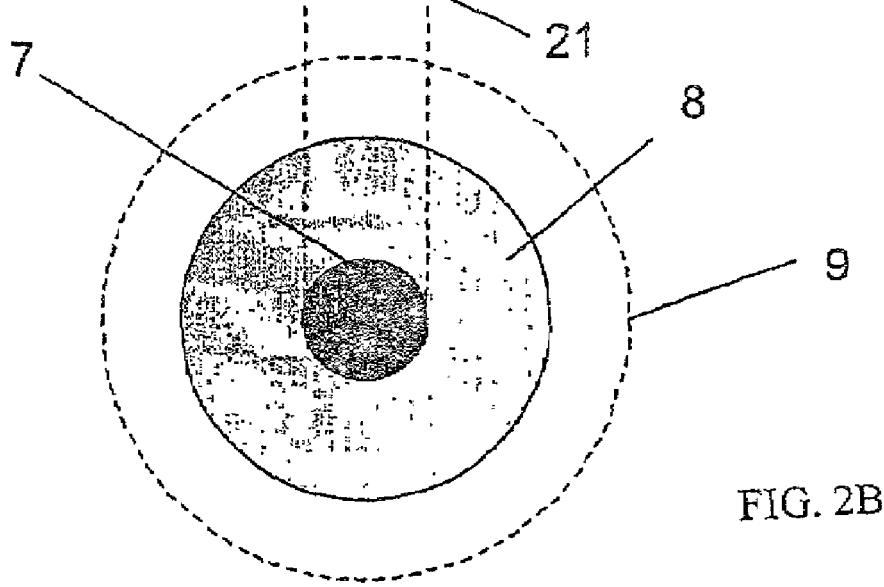
FIG. 2B is a schematic depiction of the human eye including the pupil, the iris, and the eyeball.

FIG. 2 schematically shows an eye, comprising a pupil 7, an iris 8, and an eyeball 9, in a plan view. The profile of intensity reduction 24 for a specific wavelength $\lambda$ is depicted as a function of two-dimensional area, i.e., the spectral filter 4 reduces the intensity of the particular wavelength $\lambda$ when projected onto a region $\lambda(X_0, Y_0)$ defining a specific reduced-light intensity region 21. Further, the spectral filter 4 may be configured so that the light intensity reduction is accomplished over a particular range of wavelengths, for example from 420 nm to 495 nm. Preferably, however, the range of light reduction will be from 420 nm to 470 nm and/or below 400 nm. In addition, the degree of the light intensity reduction can be varied such as, for example, between 0% and 90%. The remaining area that is not within the reduced-light intensity region 21 experiences the entire light output intensity and/or a wavelength-dependent light output.

The perimeter around the specific region in which the intensity of the light is reduced defines an absorption edge. Preferably, the absorption edges are flat, i.e., there is a clear and definitive boundary which separates the specific region in which the intensity of the light is reduced from the remainder of the cross-sectional area of the illuminating beam 2.

The spectral filter 4 may be disc-like in nature and have a light reduction profile that varies across the filter thereby defining a reduced-light intensity illumination region. For example, the light intensity reduction function of the filter 4 may vary in a graduated or stepless fashion from a central portion of the filter 4 in which the light intensity of wavelengths between 420 nm and 470 nm is reduced by up to substantially 90% (e.g., 50%) to an outer rim portion in which the light intensity in the same wavelength range is not substantially reduced.

The invention makes it possible, by way of the shape of spectral filter 4, to configure the reduced-light intensity region 21 arbitrarily in space. In addition, by mechanical displacement of the spectral filter 4 (vertically along the illuminating beam 2) and/or a displacement of illuminating optical system 3a, 3b, the reduced-light intensity region 21 can be made larger or smaller to a variable degree. Coupled with the mechanical ability to move the spectral filter 4 in its two-dimensional (x, y) plane either within the cross-sectional area of the illuminating beam 2 or completely out of the optical device, the filter 4 can be displaced three-dimensionally. Moreover, the three-dimensional movement may be controlled and monitored, for example, by a controller 25.

Although it is preferable that the (x, y) plane of the spectral filter 4 be normal to the illuminating beam, it is possible for the (x, y) plane of the spectral filter to be at an angle with respect to the illuminating beam. If the spectral filter has uniform light intensity reduction properties across its (x, y) plane, an angling of the filter 4 with respect to the illuminating beam 2 will cause a varying degree in light intensity reduction across the spectral filter 4 with respect to the objective 6. However, as previously mentioned such varying in light intensity may also be formed into the spectral filter itself.

Figure 3:
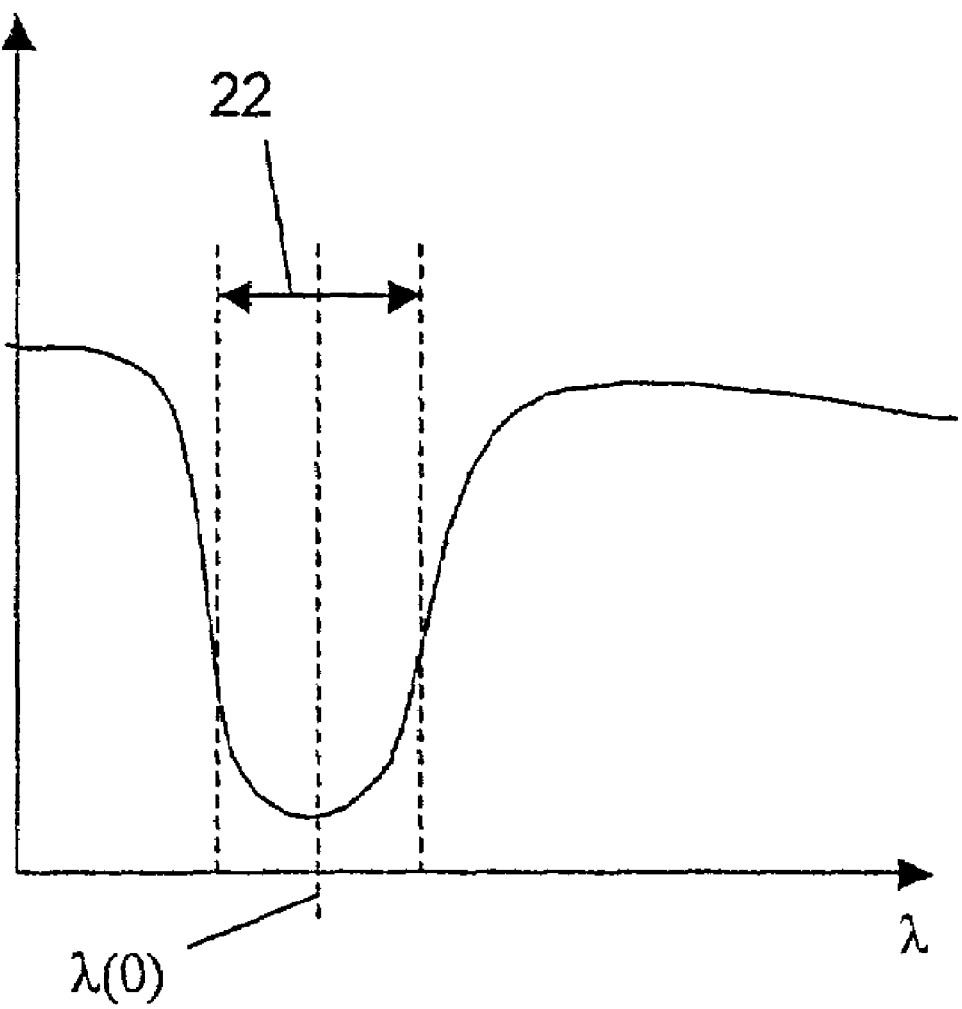
FIG. 3 shows a graph of the intensity of various wavelengths $\lambda$ at a particular location in an X-Y plane of a specimen.

As shown in FIG. 3, the absorption properties of spectral filter 4 make it possible to specifically reduce the light intensity as a function of the wavelength λ. Moreover, it is also possible to reduce the light intensity as a function of the difference in transparency in the local region of spectral filter 4. In particular, FIG. 3 shows a possible profile of the light intensity reduction as a function of the wavelength λ, with a specific reduced-light intensity wavelength region 22 at which the intensity of a specific wavelength λ(0) is reduced.

Figure 4:
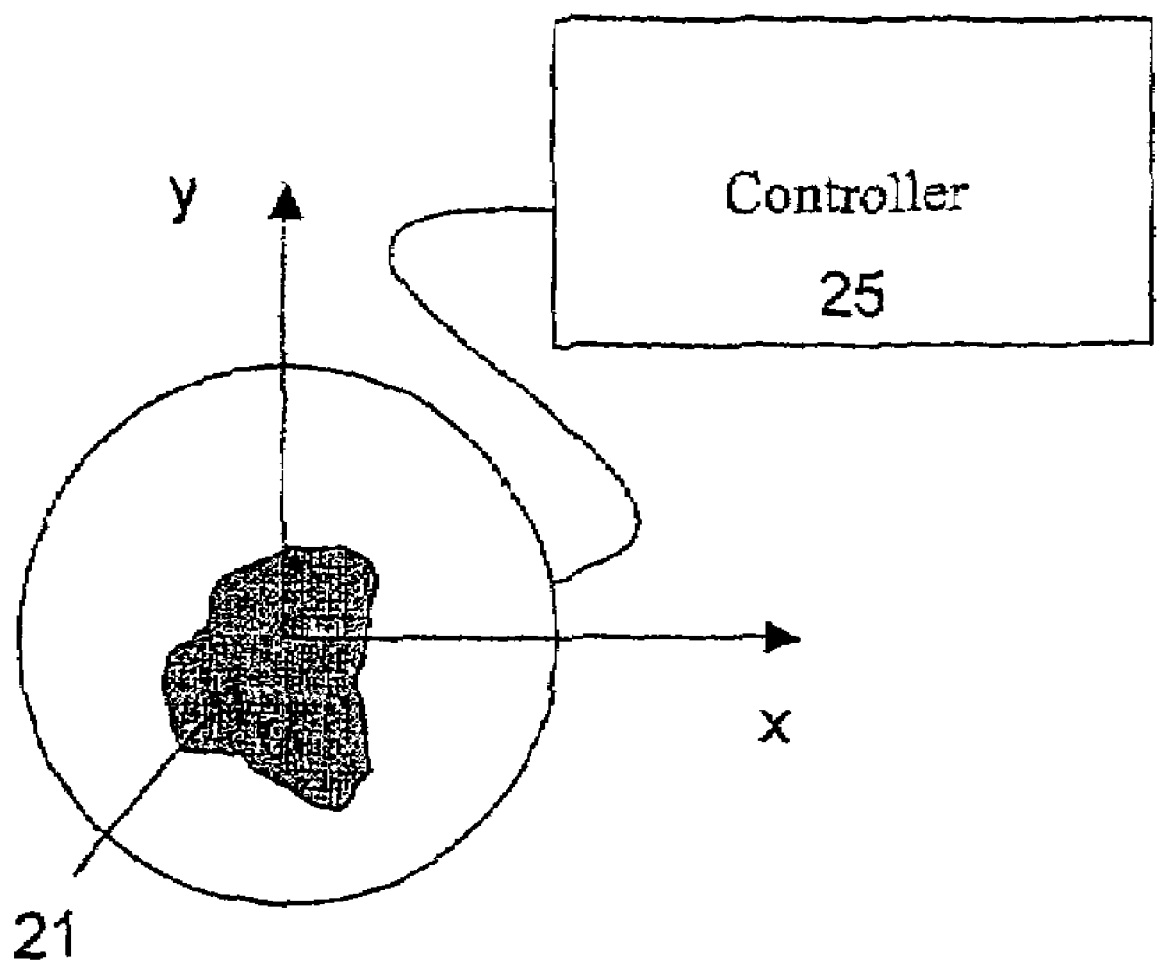
FIG. 4 is a schematic depiction of an electronic controller for a spectral filter.

A further development of the invention is the fact that the spectral filter may be configured as an LCD and/or an electrochromic film that is electronically controlled by means of a controller 25. FIG. 4 schematically shows an electronic controller 25 for the spectral filter 4, which can be configured, for example, as an electrochromic film or LCD. This facilitates controlling and varying the spatial location (x, y) of the filter 4 and thus the intensity of light transmitted to a specific region of the specimen (i.e., it allows for two-dimensional movement of the wavelength or light reducing region 21). Moreover, if the illuminating beam is reflected off of a specimen to thereby produce an image of the specimen, the movement of the spectral filter 4 can be coupled to the image such that when a particular region of the specimen moves, the filter will be correspondingly moved.

Although reference is made in the above text to a surgical microscope, the invention is nevertheless not limited thereto but rather is also open to other users of optical devices with a partial reduction in the illumination intensity and/or specimen irradiation (e.g., projectors, video and photographic cameras, etc.). In addition, it will be apparent to those skilled in the art that various modifications and variations can be made to the disclosed preferred embodiments of the present invention without departing from the scope or spirit of the invention. Accordingly, it should be understood that the apparatus described herein is illustrative only and is not limiting upon the scope of the invention, which is indicated by the following claims.

What is claimed is:

1. An optical devices comprising:
  a housing, the housing comprising:
    a light source emitting light along an illuminating beam having a two-dimensional cross-sectional area;
    a main objective; and
    a spectral filter positioned between the light source and the main objective,
    wherein the spectral filter is adapted to reduce, without eliminating, the intensity of the light emitted by the light source in a specific region, the specific region being a subsection of the two-dimensional cross-sectional area of the illuminating beam;
  wherein the optical device is a surgical microscope.

2. The device according to claim 1, wherein the reduction of the light intensity by the spectral filter is wavelength-dependent.

3. The device according to claim 1, wherein the reduction of the light intensity by the spectral filter is intensity-dependent.

4. The device according to claim 3, wherein the reduction of the light intensity by the spectral filter is also wavelength-dependent.

5. The device according to claim 1, wherein at least one region of the spectral filter is configured to absorb a portion of the intensity produced by a specific wavelength λ which is in a range selected from the group consisting of the wavelengths from 420 to 470 nm, wavelengths below 400 nm, wavelengths injurious to a human's retina, and wavelengths injurious to a human's cornea.

6. The device according to claim 2, wherein the spectral filter is configured to absorb a portion of the light being transmitted by the light source having at least one wavelength, and wherein for each wavelength, a portion of which is absorbed, absorption edges are defined between the specific region and the remainder of the cross-sectional area of the illuminating beam.

7. The device according to claim 6, wherein the absorption edges of at least one of the reduced-light intensity wavelengths are flat.

8. The device according to claim 1, wherein the spectral filter has a profile that has reduced-light intensity wavelength regions which vary from a central portion of the spectral filter to an outer rim of the spectral filter.

9. The device according to claim 8, wherein in the central portion, the intensity of wavelengths between 420 nm and 470 nm is reduced by substantially 90%, and wherein in the outer rim, the intensity of the wavelengths between 420 nm and 470 nm is not substantially reduced.

10. The device according to claim 8, wherein in the central portion, the intensity of wavelengths between 420 nm and 470 nm is reduced by substantially 50%.

11. The device according to claim 10, wherein in the outer rim, the intensity of the wavelengths between 420 nm and 470 nm is not substantially reduced.

12. The device according to claim 1, wherein the light source is configured to produce light having wavelengths between 420 nm and 470 nm, and wherein the spectral filter reduces the intensity of the light emitted by the light source by between substantially 0% and 90%.

13. The device according to claim 1, wherein the spectral filter has a disk-like shape with a variable reduced-light intensity illumination region.

14. The device according to claim 1, wherein the spectral filter is adapted to be mechanically moved into and out of the illuminating beam of the device.

15. The device according to claim 14, wherein the illuminating beam is adapted to be projected through the objective and onto a specimen.

16. The device according to claim 1, wherein the spectral filter defines an x, y plane, and wherein the spectral filter is adapted to be moved horizontally along its x, y plane.

17. The device according to claim 16, wherein the spectral filter is adapted to be vertically displaced along the illuminating beam.

18. The device according to claim 16, wherein the spectral filter is adapted to be moved so that the size of the specific region can be altered.

19. The device according to claim 18, wherein the movement of the spectral filter can be controlled electronically or manually.

20. The device according to claim 1, wherein the spectral filter defines an (x, y) plane which is non-normal to the illuminating beam thereby causing a varying degree in light intensity reduction across the spectral filter with respect to the objective.

21. The device according to claim 1, wherein the spectral filter is any one or more of a thin film, an LCD, and an electrochromic film.

22. The device according to claim 15, further comprising: a control circuit configured to control spatial displacement of the spectral filter.

23. The device according to claim 1, wherein the spectral filter is movable in an up-and-down direction between the light source and the main objective, along a path of the illuminating beam.

24. The device according to claim 1, wherein a path of the illuminating beam from the light source to the main objective is substantially linear.

25. The device according to claim 1, further comprising:
at least one viewer,
wherein the at least one viewer is configured to receive a return beam that is not co-linear with the illuminating beam.

26. A surgical microscope comprising:
an optical device housing comprising:
a light source emitting light along an illuminating beam having a two-dimensional cross-sectional area;
a main objective;
a spectral filter that is configured to be positioned between the light source and the main objective, wherein the spectral filter is:
(a) adapted to reduce, without eliminating, the intensity of the light emitted by the light source in a specific region, the specific region being a subsection of the two-dimensional cross-sectional area of the illuminating beam; and
(b) configured to be displaced vertically and/or horizontally when positioned between the light source and the main objective; and
a control circuit configured to control the vertical and/or horizontal displacement of the spectral filter.

27. The microscope according to claim 26, wherein the reduction of the light intensity by the spectral filter is wavelength-dependent.

28. The microscope according to claim 26, wherein the reduction of the light intensity by the spectral filter is intensity-dependent.

29. The microscope according to claim 28, wherein the reduction of the light intensity by the spectral filter is also wavelength-dependent.

30. The microscope according to claim 26, wherein at least one region of the spectral filter is configured to absorb a portion of the intensity produced by a specific wavelength λ which is in a range selected from the group consisting of the wavelengths from 420 to 470 nm, wavelengths below 400 nm, wavelengths injurious to a human's retina, and wavelengths injurious to a human's cornea.

31. The microscope according to claim 27, wherein the spectral filter is configured to absorb a portion of the light being transmitted by the light source having at least one wavelength, and wherein for each wavelength, a portion of which is absorbed, absorption edges are defined between the specific region and the remainder of the cross-sectional area of the illuminating beam.

32. The microscope according to claim 26, wherein a path of the illuminating beam from the light source to the main objective is substantially linear.

33. The microscope according to claim 26, further comprising:
at least one viewer,
wherein the at least one viewer is configured to receive a return beam that is not co-linear with the illuminating beam.

34. The microscope according to claim 26, wherein at least a portion of a central region of the light emitted by the light source is incident on the main objective.

35. An optical device, comprising:
a housing, the housing comprising:
a light source emitting light along an illuminating beam having a two-dimensional cross-sectional area;
a main objective; and
a spectral filter positioned between the light source and the main objective,
wherein the spectral filter is adapted to reduce, without eliminating, the intensity of the light emitted by the light source in a specific region, the specific region being a subsection of the two-dimensional cross-sectional area of the illuminating beam;
wherein at least a portion of a central region of the light emitted by the light source is incident on the main objective.

* * * * *